(12) United States Patent
Matthison-Hansen

(10) Patent No.: US 11,109,745 B2
(45) Date of Patent: Sep. 7, 2021

(54) ENDOSCOPE

(71) Applicant: AMBU A/S, Ballerup (DK)

(72) Inventor: Kaspar Mat Matthison-Hansen, Helsingør (DK)

(73) Assignee: AMBU A/S, Ballerup (DK)

(*) Notice: Subject to any disclaimer, the term of this patent is extended or adjusted under 35 U.S.C. 154(b) by 372 days.

(21) Appl. No.: 16/367,218

(22) Filed: Mar. 27, 2019

(65) Prior Publication Data

US 2019/0216294 A1    Jul. 18, 2019

Related U.S. Application Data

(63) Continuation of application No. PCT/DK2017/050318, filed on Sep. 29, 2017.

(51) Int. Cl.
*A61B 1/00* (2006.01)
*A61B 1/005* (2006.01)
(Continued)

(52) U.S. Cl.
CPC .......... *A61B 1/0051* (2013.01); *A61B 1/008* (2013.01); *A61B 1/0052* (2013.01);
(Continued)

(58) Field of Classification Search
None
See application file for complete search history.

(56) References Cited

U.S. PATENT DOCUMENTS

| 609,570 A | 8/1898 | Bowden |
| 3,897,775 A * | 8/1975 | Furihata ............ A61B 1/015 600/131 |

(Continued)

FOREIGN PATENT DOCUMENTS

| CN | 201189183 | 2/2009 |
| CN | 101516273 | 8/2009 |

(Continued)

OTHER PUBLICATIONS

International Preliminary Report on Patentability received for PCT Patent Application No. PCT/DK2017/050318, dated Apr. 11, 2019, 7 pages.

(Continued)

*Primary Examiner* — Timothy J Neal
(74) *Attorney, Agent, or Firm* — Faegre Drinker Biddle & Reath LLP

(57) ABSTRACT

An endoscope having a proximal end, a distal end, a handle, and an insertion tube that terminates in a tip section. The tip section includes a bending section and an articulated tip part, and the bending section includes articulated segments, each articulated segment including a guide passage for a control member. The proximal end of the elongated control member is attached to an operating member arranged at the handle and the distal end of the elongated control member is attached to the most distal articulated segment of the bending section. An intermediate section of the elongated control member passes through said guide passages. The intermediate section has a reduced overall cross-sectional area as compared to the majority of said elongated control member.

15 Claims, 7 Drawing Sheets

(51) Int. Cl.
*A61B 1/008* (2006.01)
*A61B 1/018* (2006.01)

(52) U.S. Cl.
CPC .......... *A61B 1/0056* (2013.01); *A61B 1/0057* (2013.01); *A61B 1/00103* (2013.01); *A61B 1/00135* (2013.01); *A61B 1/018* (2013.01); *A61B 1/0008* (2013.01)

(56) References Cited

U.S. PATENT DOCUMENTS

| | | | |
|---|---|---|---|
| 5,284,128 | A | 2/1994 | Hart |
| 5,976,075 | A | 11/1999 | Beane |
| 2003/0135156 | A1 | 7/2003 | Bencini et al. |
| 2004/0059257 | A1 | 3/2004 | Gaber |
| 2004/0167436 | A1 | 8/2004 | Reynolds et al. |
| 2005/0004515 | A1 | 1/2005 | Hart et al. |
| 2005/0256452 | A1* | 11/2005 | DeMarchi ......... A61M 25/0138 604/95.04 |
| 2008/0065116 | A1 | 3/2008 | Lee et al. |
| 2008/0255446 | A1 | 10/2008 | Akins |
| 2008/0300462 | A1* | 12/2008 | Intoccia ............... A61B 1/0052 600/146 |
| 2008/0319418 | A1 | 12/2008 | Chong |
| 2009/0192495 | A1* | 7/2009 | Ostrovsky ......... A61M 25/0147 604/528 |
| 2010/0191150 | A1 | 7/2010 | Palme, Jr. et al. |
| 2011/0184232 | A1* | 7/2011 | Maxwell .......... A61B 17/00234 600/104 |
| 2011/0196204 | A1 | 8/2011 | Setty et al. |
| 2013/0096384 | A1* | 4/2013 | Arai ..................... A61B 1/0055 600/144 |
| 2014/0023428 | A1 | 1/2014 | Kappel et al. |
| 2014/0379000 | A1 | 12/2014 | Romo et al. |
| 2015/0057537 | A1 | 2/2015 | Dillon et al. |
| 2015/0272425 | A1 | 10/2015 | Ueda |
| 2015/0335227 | A1 | 11/2015 | Jacobsen et al. |
| 2015/0366436 | A1 | 12/2015 | Iuel |
| 2016/0325077 | A1* | 11/2016 | Yamanaka ............. A61B 34/71 |

FOREIGN PATENT DOCUMENTS

| | | |
|---|---|---|
| CN | 102164546 | 8/2011 |
| CN | 103298414 | 9/2013 |
| CN | 105473048 | 4/2016 |
| CN | 105899116 | 8/2016 |
| EP | 2313007 | 4/2011 |
| EP | 2923633 A1 | 9/2015 |
| EP | 3100666 A1 | 12/2016 |
| JP | 08-131441 A | 5/1996 |
| WO | WO01/078825 | 10/2001 |
| WO | WO2004/096015 | 11/2004 |
| WO | WO2004/103430 | 12/2004 |
| WO | WO2005/094661 | 10/2005 |
| WO | WO2012/040233 | 3/2012 |
| WO | WO2014/106511 | 1/2014 |
| WO | WO2014/127780 | 8/2014 |
| WO | 2015/115196 A1 | 8/2015 |
| WO | WO2016/037133 | 3/2016 |

OTHER PUBLICATIONS

International Search Report and Written Opinion received for PCT Patent Application No. PCT/DK2017/050318, dated Dec. 13, 2017, 8 pages.
Office action in related Chinese patent application CN201780059023.1, dated Apr. 6, 2021, 8 pgs. (translation included).
Search report in related Danish application No. PA 2016 70776 dated Dec. 22, 2016; 7 pgs.
Communication pursuant to Article 94(3) EPC issued in EP 17 779 998.8, dated Sep. 11, 2020, 4 pages.

* cited by examiner

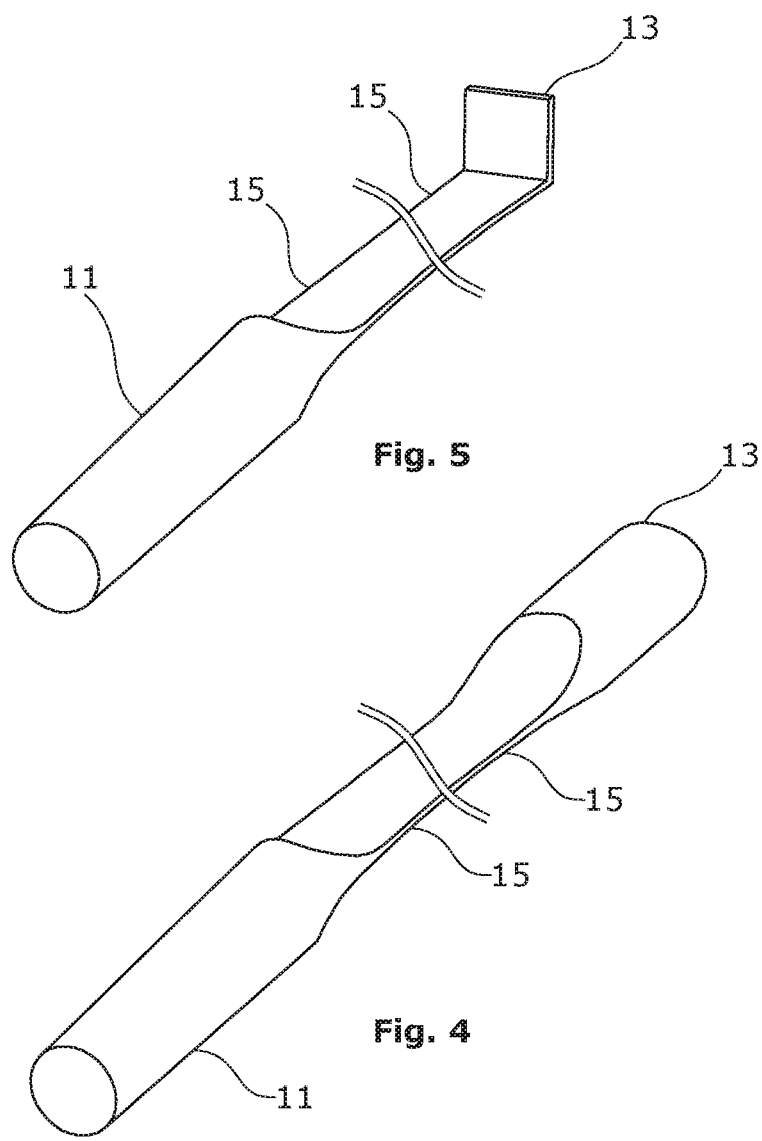

ENDOSCOPE

CROSS-REFERENCE TO RELATED APPLICATIONS

This patent application is a continuation International Application No. PCT/DK2017/050318, filed Sep. 29, 2017, which claims the benefit of Denmark Patent Application No. PA 2016 70776, filed Sep. 30, 2016; both applications are incorporated by reference herein in their entirety.

TECHNICAL FIELD

The present invention relates to an endoscope, in particular but not exclusively a disposable endoscope, and more specifically to the bending section at the distal tip of the endoscope.

BACKGROUND

Endoscopes are well known devices for visually inspecting inaccessible places such as human body cavities. Typically, the endoscope comprises an elongated insertion tube with a handle at the proximal end as seen from the operator and visual inspections means, such as a built in camera, at the distal end of the elongated insertion tube. This convention of distal and proximal, proximal being the end closest to the operator and distal being the end remote from the operator, as used above for the endoscope in general will, where applicable, be adhered to for all parts throughout this description. Electrical wiring for the camera and other electronics such as LED lighting run along the inside of the elongated insertion tube from the handle to the tip at the distal end. Instead of using cameras, endoscopes may also be fiber-optic, in which case the optical fibers run along inside of the elongated insertion tube. Also, a working channel may run along the inside of the insertion tube from the handle to the tip, e.g. allowing liquid to be removed from the body cavity or allowing the insertion of surgical instruments or the like into the body cavity.

Furthermore, in order to be able to maneuver the endoscope inside the body cavity, the endoscope may comprise a section with increased flexibility, in the following referred to as the bending section. The bending section normally comprises a number of articulated segments, of which the most distal segment may constitute the tip part of the endoscope. The tip part comprises light source, camera, working and suction channels etc. as mentioned above. It is commonly known to control the bending section at the distal end of an endoscope, i.e. the section adjacent the distal tip of the insertion tube of the endoscope, by means of Bowden cable pulls.

Typically, this is done by tensioning or slacking a number of push-pull wires in a corresponding number of guide tubes also running along the inside of the elongated insertion tube from the last segment of the bending section, e.g. constituted by the tip part, where they are attached to a control mechanism with a control knob in the handle in an arrangement commonly known as a Bowden cable, cf. Bowden's original U.S. Pat. No. 609,570. This allows the operator to bend the bending section and point the tip part in a desired direction. The Bowden cables are arranged with an offset with respect to the center axis of the bending section, so as to allow the bending section to bend in one direction upon pulling forces to the last segment.

An endoscope of the kind outlined above is inter alia described in the prior art document WO2014/127780. In this document, drawbacks related to the use of Bowden cables in disposable endoscopes, which must by nature not be costly to manufacture, are disclosed. These drawbacks relate to the use of a plastic tube as the guide tube of the Bowden cable, which prevents the flexible cable from buckling under push, and thus ensures the transmission of force from the knob of the control mechanism to the bending section.

A further drawback by the use of Bowden cables not addressed by WO2014/127780 is the fact that the Bowden cable, and in particular the guide tube thereof, takes up precious space in the insertion tube. The insertion tube must be kept as narrow as possible in order to better access the area of interest, such as a body cavity, and yet have room for cables, wires, channels etc. including the control cables for the bending section. One way of doing so is to use only one control cable rather than two. Two control cables have the advantage that only pulling forces need to be applied, and there is therefore not the same risk of the control cable buckling under push, as compared to when only a single Bowden cable is used. Such buckling is undesired because it reduces the maximum deflection of the bending section, and thus the maneuverability of the distal tip of the endoscope.

US2011/0196204 discloses a shape-conforming intubation device with an articulated tip. It is suggested that as an alternative to a pull-wire a push-rod may be used to control the articulated tip, but the push-rod is not dealt with as such and no details are given.

Based on this prior art it is the object of the present invention to provide an improved force transfer mechanism for operating the bending section of an endoscope which overcomes the above drawbacks.

SUMMARY

An endoscope is provided herein which has a force transfer member that provides good deflection of the bending section, takes up little space, has low cost, and allows the endoscope to have a long shelf life. According to some embodiments, the endoscope has a proximal end and a distal end, said endoscope comprising a handle at the proximal end and an insertion tube extending from the handle towards the distal end, said insertion tube terminating in a tip section at distal end, where the tip section comprises a bending section and an articulated tip part where the bending section comprises a number of articulated segments, wherein each segment of said number of articulated segments comprises a guide passage for a control member, and an elongated control member having a proximal end and a distal end, where the proximal end of the elongated control member is attached to an operating member arranged at the handle and the distal end of the elongated control member is attached to the most distal articulated segment of the bending section, and an intermediate section of the elongated control member between said proximal end of the elongated control member and the distal end of the elongated control member passes through said guide passages, characterized in that said intermediate section has a reduced overall cross-sectional area as compared to the majority of said elongated control member.

By reducing the overall cross-sectional area of a part of the elongated control member, this part becomes more flexible than the remainder of the elongated control member and will therefore be more likely to buckle under compression forces and bend under tension, thereby bending the bending section in one or the other direction.

According to a first preferred embodiment, the distal end of the elongated control member also comprises a reduced cross-sectional area, said distal end being deformed to a predetermined shape for securing the engagement with the most distal articulated segment. In manufacturing the endoscope, this allows the area with the reduced cross-sectional area to be easily inserted into the guide passages of the bending section, then deforming the distal end thereof into a shape aiding in ensuring good fixation of the distal end of the elongated control member in the most distal articulated segment.

According to a further preferred embodiment, the articulated tip part constitutes the most distal articulated segment of the bending section. This allows the bending section of the endoscope to be as close as possible to the distal end of the endoscope, which for many types of endoscopes is highly desirable, e.g. for reasons of manoeuvrability.

According to another preferred embodiment, the elongated control member is made of metal. Metal has good properties in withstanding and transmitting both compressive forces and tension.

In a particularly preferred embodiment, the elongated control member comprises a rod. Using a rod aids in providing the desired properties, in particular in terms of withstanding and transmitting both compressive forces and tension.

According to another preferred embodiment, the elongated control member comprises a tube with a collapsed part so as to provide said reduced cross-sectional area. Manufacturing the elongated control member this way is advantageous, because all that is needed it to cut a desired length of tube, and then using a suitable compressing tool flattening the desired part of the tube, in order to obtain a reduced overall cross-sectional area.

According to a further preferred embodiment, the majority of the length of elongated control member is covered with a coaxial sheath. Using such a sheath prevents the elongated control member from rubbing against and potentially damage other parts inside the insertion tube, even if the sheath is very thin.

According to yet a further embodiment, guide means are provided co-axially with the elongated control member and said sheath at or adjacent the proximal end of the elongated control member. These will serve to keep the proximal end of the sheath and the elongated control member in parallel, when during operation of control lever a rotary motion is imparted on the proximal end of the elongated control member. Thus, the rim of the opening at the proximal end of the sheath will be less prone do damage from the elongated control member, because the two parts are kept in parallel, and the elongated control member thus does not exert a force on the rim.

According to another embodiment, the working channel and the sheath comprise an integral member, e.g. an extruded multi-lumen tubing. This ensures the fixation of the sheath with respect to other part inside the insertion tube. Accordingly, the sheath will remain stationary and not rub against the other parts, even when subject to frictional forces from the elongated control member moving inside it.

BRIEF DESCRIPTION OF THE DRAWINGS

The invention will now be described in greater detail based on non-limiting exemplary embodiment, and with reference to the schematic drawings, on which:

FIG. 4 shows a detail of the distal end of the elongated control member of FIG. 2, FIG. 5 shows a detail of the distal end of the elongated control member of FIG. 3.

DETAILED DESCRIPTION

Figure 1:
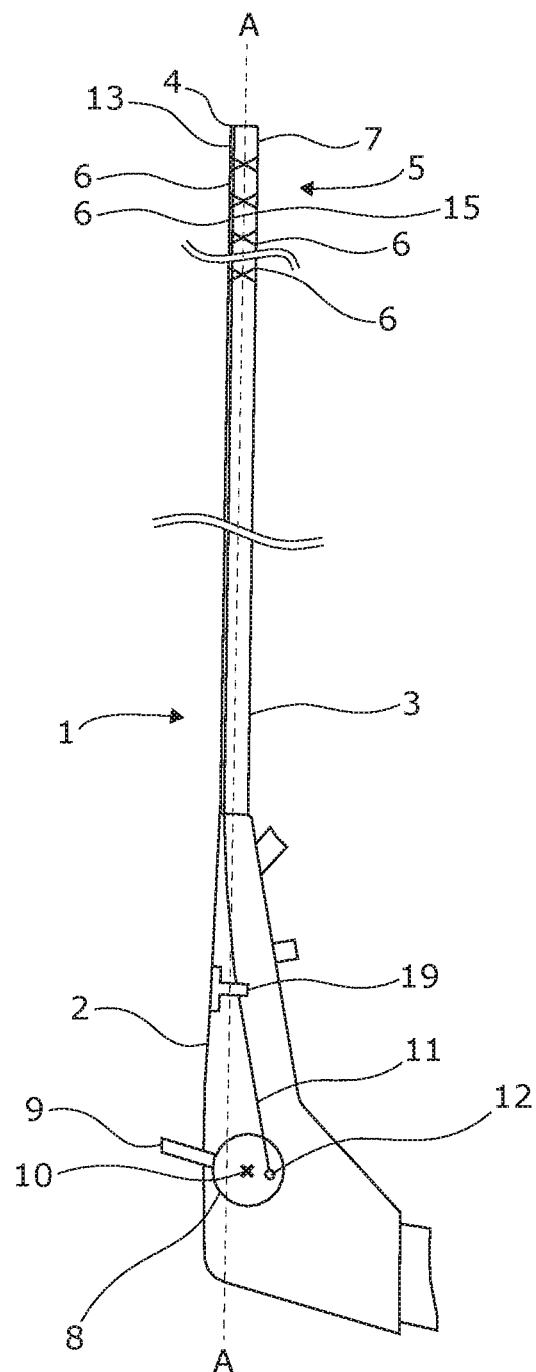
FIG. 1 shows a schematic longitudinal cross-section of an endoscope according to the invention.

Turning first to FIG. 1 a longitudinal cross-section of an endoscope 1 is schematically shown. The endoscope 1 comprises an ergonomically shaped handle 2 forming the proximal end of the endoscope 1. An insertion tube 3 extends from the handle 2 towards the distal end 4 of the endoscope 1. At or in conjunction with the distal end 4, the endoscope 1 comprises a bending section 5, forming part of the tip section. The bending section comprises a number of articulated segments 6, 7. The most distal articulated segment 7 of the bending section preferably comprises an articulated tip part of the endoscope 1, in which tools, camera, illumination etc. are located along with various passages, such as suction and working channels terminating at the distal end 4 of the endoscope 1.

In the handle 2 an operating member 8 with a lever 9, which may be digitally manipulated, e.g. by the thumb of an operator, is located. In the illustrated embodiment the operating member 8 is rotatable with respect to the handle 2 about an axis 10. A first proximal end of an elongated control member 11 is attached to the operating member 8 at a location generally opposite the lever 9. The skilled person, however, will understand that the location of the attachment point 12 on the operating member is more or less a matter of choice as long as there is a sufficient distance from the axis 10 to provide the necessary displacement, torque and resulting force on the elongated control member 11. The distal end 13 of the elongated control member 11 is secured to the most distal articulated segment of the bending section 5, in the illustrated example comprised of the tip part 7 of the endoscope 1. The remainder of the articulated segments 6 are provided with guide passages 14, 14', best seen in FIGS. 2 and 3, which in the neutral configuration are aligned on a straight line. An intermediate section 15 of the elongated control member 11 between said proximal end of the elongated control member 11 and the distal end 11 of the elongated control member 11 passes through said guide passages 14, 14'.

In the illustrated example of FIG. 1, the endoscope 1 is in a neutral or resting configuration. That is to say no external forces, including force on the lever 9 of the operating member 8, are influencing the curvature of the insertion tube 3 and the bending section 5. In this neutral configuration the insertion tube 3 and the bending section 5 are straight along a common central axis A.

As can be seen, the elongated control member 11 has an offset with respect to the central axis A in the bending section. Thus, when applying a torque to the lever 9 of the operating member 8 the resulting displacement force causes the articulated members 6, 7 to bend in one or the other direction. In the illustrated example the bending section will bend upwardly (in the drawing) if the displacement force is a pull force, and downwardly if the displacement force is a pushing force. This is merely a matter of example, and the skilled person will understand that the deflection direction is a matter of choice, depending on where in the cross-section of the bending section the guide passages 14 are located. Deflection could thus also be out of the plane of the drawing. Accordingly, deflection of the distal tip part 7 in two opposite directions by bending the bending section 5 can be achieved with only a single elongated control member 11. This saves space in the distal tip part 7 and the bending section 5 in general.

Figure 2:
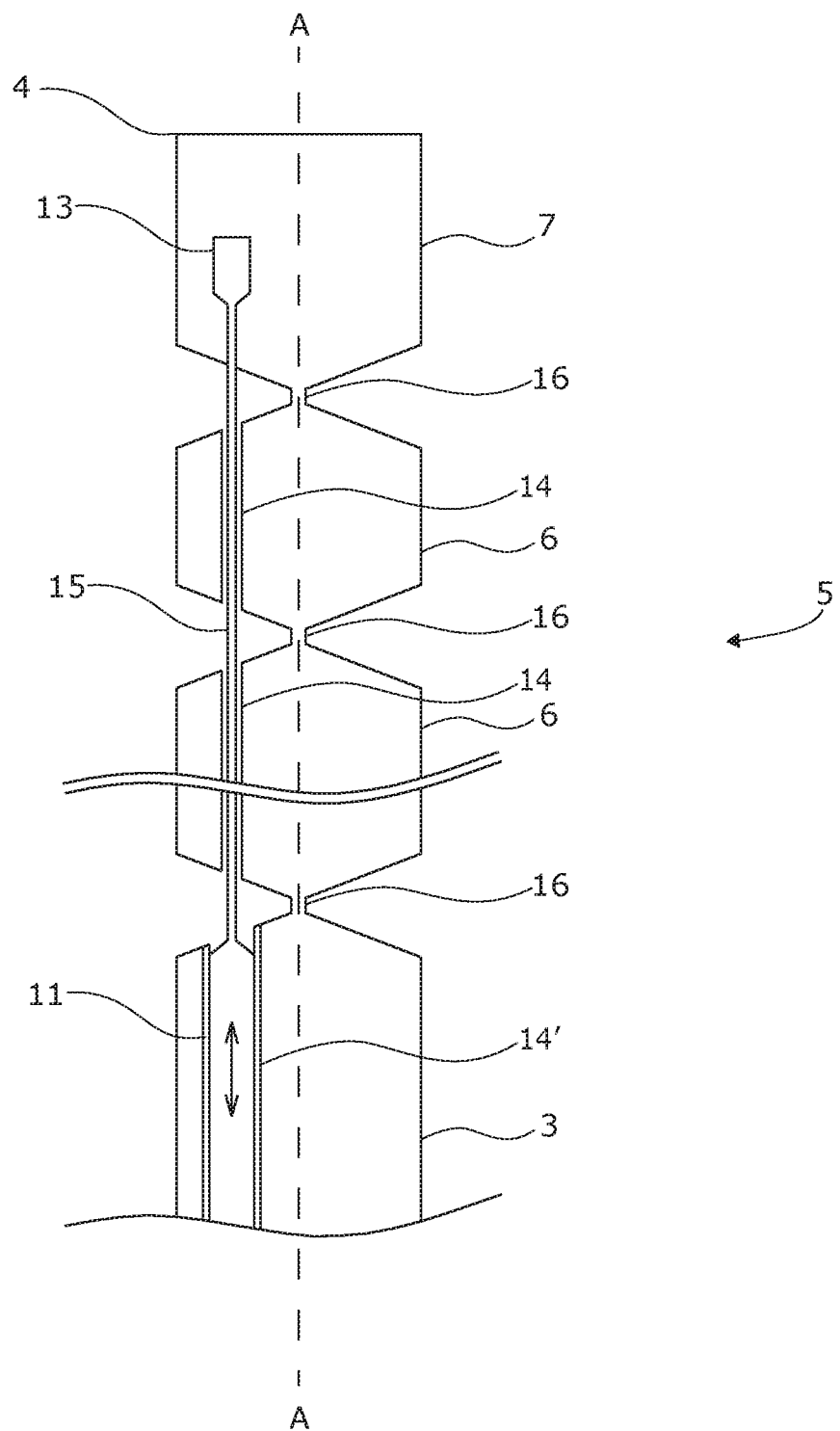
FIG. 2 shows parts of the bending section and a first embodiment of the elongated control member.
Figure 3:
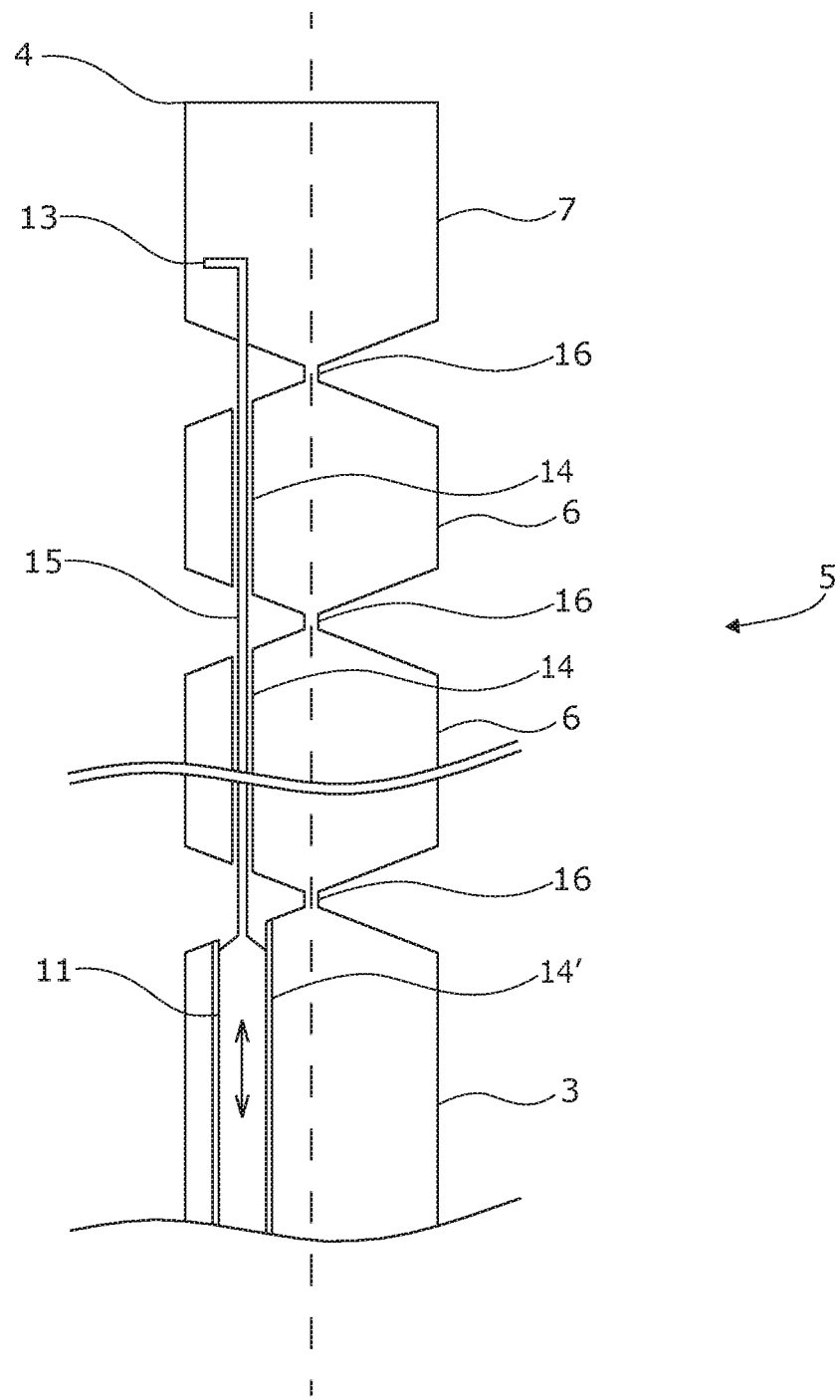
FIG. 3 shows parts of the bending section and a second embodiment of the elongated control member.

FIGS. 2 and 3 schematically show different embodiments of elongated control members 11 in the bending section 5. The elongated control member 11 is preferably a rod of a suitably rigid material such as metal or a metal alloy, in particular steel. As can be seen the overall cross-sectional dimensions of the elongated control member 11 vary along the length thereof. The majority of the elongated control member 11, a part of which can be seen at the left-hand side of FIGS. 2 and 3, has a first cross-section, preferably circular. In FIG. 2 the distal end 13 of the elongated control member 11 has the same cross-section as the first cross-section, in order to provide a means for securing the distal end 13 in the distal tip part 7 of the endoscope 1. As can be seen, the elongated control member 11 comprises a narrower intermediate part 15 between the proximal end and the distal end 13. This narrow intermediate part 15 is preferably the same width as the cross-section of the majority part of the elongated control member 11 but has a substantially reduced thickness, cf. also FIG. 4.

This narrower intermediate part 15 provides the elongated control member 11 with a high degree of flexibility, so as not to impede the bending of the bending section 5. Since the guide passages 14 have a width and height corresponding to the cross-section of the intermediate part 15 of the elongated control member 11, the elongated control member 11 is prevented from buckling, and thus ensures good force transmission to the distal end part 13 thereof. In this respect, it should be noted that the gaps illustrated between the elongated control member 11 and the walls of the guide passages 14, 14' are exaggerated for illustration. The gaps are not so narrow that they impede the sliding motion of the elongated control member 11 with respect to the articulated members 6. In any case the narrow intermediate part 15 of the elongated control member and the passages for it takes up much less space in the bending section than the full cross-section of the majority part of the elongated control member would, let alone two parts for a push-pull arrangement.

FIG. 3 essentially corresponds to FIG. 2 only the termination and securing of the distal end 13 of the elongated control member 11 in the distal tip part 7 differ. More specifically, rather than having the full cross-section of the majority part, or at least an increased cross-section as compared to that of the narrow intermediate part 15, the narrow cross-section continues all the way to the distal end 13 of the elongated control member 11. At the distal end 13 of the elongated control member 11 the narrow cross-section is suitably deformed to engage and be secured to the distal tip part 7. The deformation may be any suitable deformation, but in practice a single bend of ninety degrees as illustrated will suffice, cf. also FIG. 5. This has the advantage that during manufacture the narrow part 15 of the elongated control member 11 may be introduced through the passages 14 from the proximal end towards distal end and into the distal tip part 7. Only then is the distal end part 13 of the elongated control member 11 deformed to secure its position with respect to the distal tip part 7. Preferably, the position is further secured by means of an adhesive or by moulding resin around it. The latter is convenient since normally resin is already used to secure other parts of the endoscope 1 in the distal tip part 7, in particular but not exclusively the abovementioned camera and other electronics such as LED lighting, as well as the distal ends of tubes forming working and suction channels. These parts are not relevant for the present invention and have largely been omitted for illustration purposes.

In the illustrated embodiments, the articulation between the articulated segments 6, 7 are provided by means of foil hinges 16, but the skilled person will understand that other hinges or articulation means may be used instead.

Figure 6:
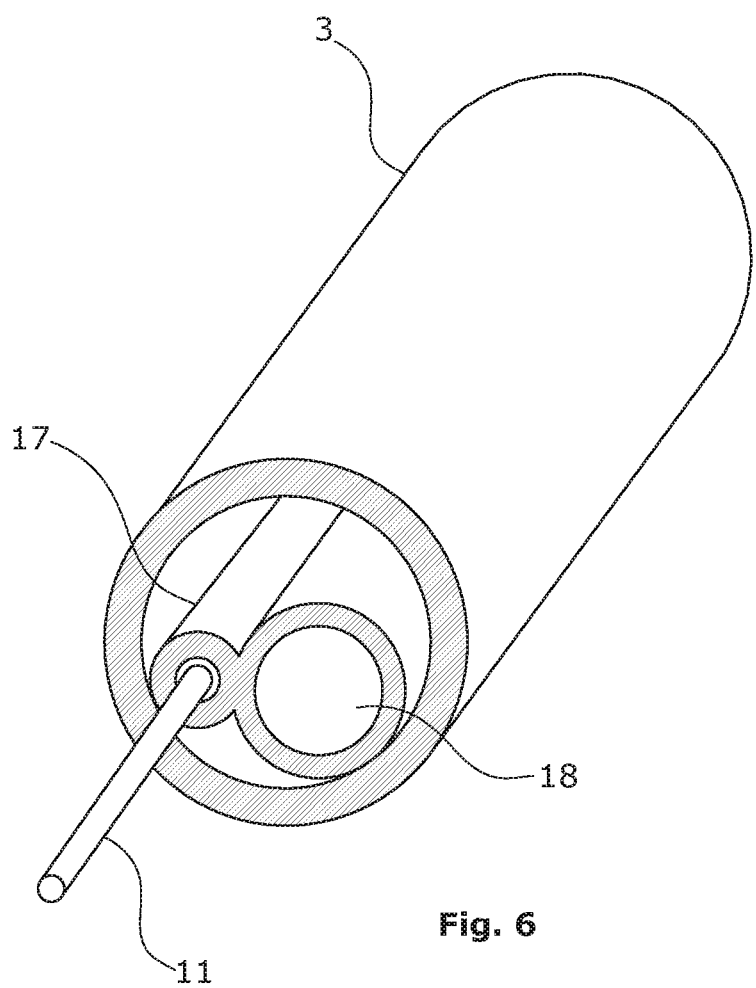
FIG. 6 shows a part of the elongated control member passing through a section of the insertion tube of an endoscope according to the invention, FIG. 7 schematically shows a first embodiment of the linkage between the elongated control member and the operating member, and FIG. 8 schematically shows a second embodiment of the linkage between the elongated control member and the operating member.
Figure 7:
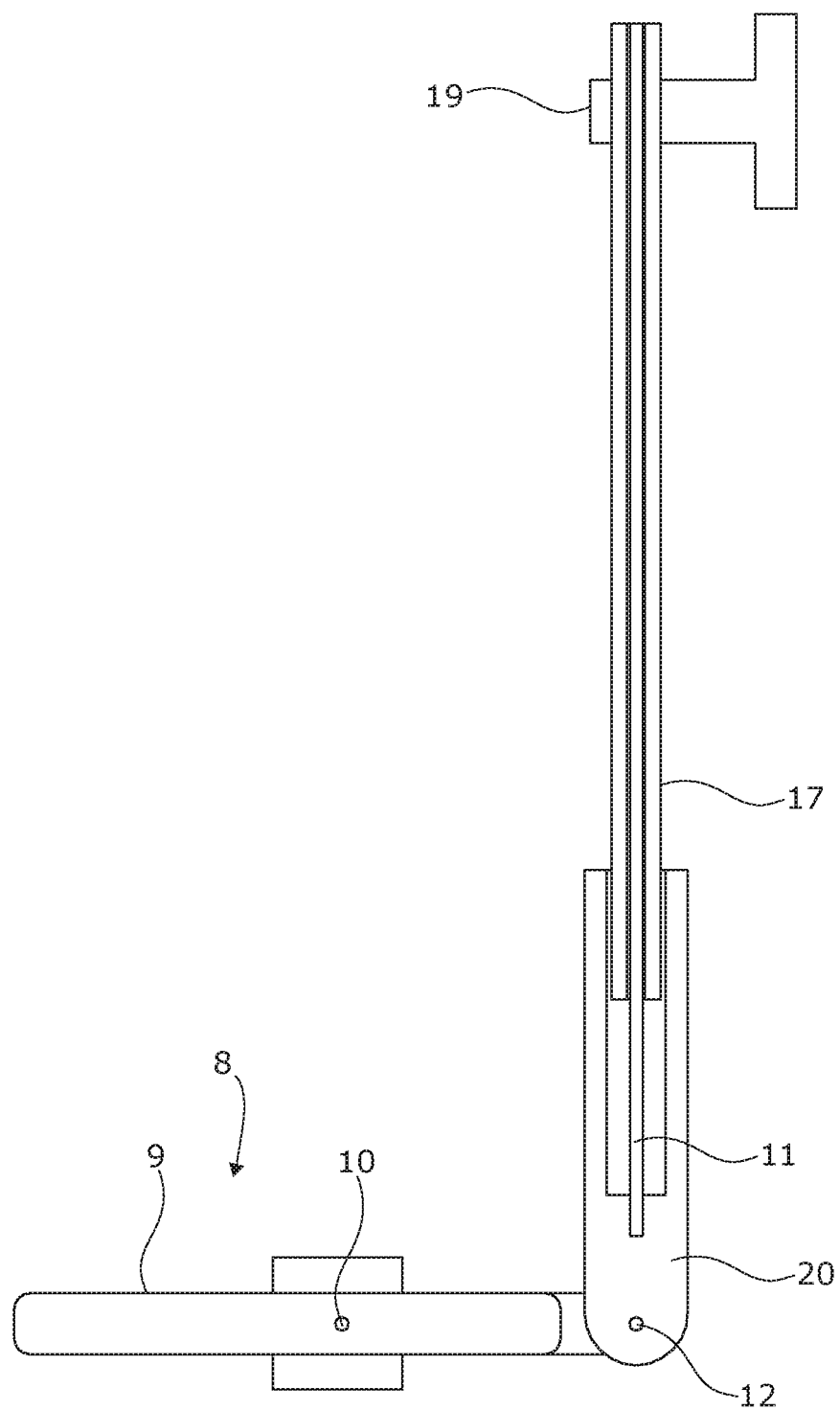

Turning now to FIGS. 6 and 7, it can be seen that in the handle 2 and in the majority of the insertion tube 3, more specifically between the handle 2 and the bending section 5, the elongated control member 11 may be surrounded by an optional sheath 17. The sheath 17 is coaxial with the elongated control member 11 and covers the majority of its length. The sheath 17 serves dual purposes. One is that it prevents the elongated control member 11 from rubbing against other parts that are located in the handle 2 and the insertion tube 3, such as the tube providing the working channel 18, and electrical cables and wires (not shown). Such rubbing is undesirable as it involves a risk of damage to these other parts. The second purpose is that it confers further rigidity to the elongated control member 11 preventing it from buckling in the handle 2 and the insertion tube 3. Unlike the guide tube of a Bowden cable, the sheath 17 need not be secured in position but could in principle just lie floatingly in the handle 2 and insertion tube 3. Since, however, there would be a risk of the sheath 17 moving along with the elongated control member 11, and in turn rub against the above-mentioned other parts, it is preferable to provide a fixation or holder 19, which secures the position of the sheath 17 with respect to the handle housing 2 as illustrated in FIGS. 1 and 7, or other part of the endoscope 1. As illustrated in FIG. 6, the sheath 17 and working channel 18 may preferably be provided in the same integral member, in particular by providing them in an extruded multi-lumen tubing, in order to further reduce the number of parts and prevent parts to rub against each other. Alternatively, to prevent the sheath 17 to move along with the elongated control member 11, the sheath 17 may be attached to the working channel 18 at distinct points such as by provision of an adhesive or a fasting member like a clip or a buckle. Such holders 19 could also be used to directly secure the position of the elongated control member 11, i.e. without the optional sheath 17. Since, space is sparse in the insertion tube 3, the optional sheath 17 may also only have the protective function, because the other parts in the insertion tube 3 will support the elongated control member 11 against buckling.

Figure 8:
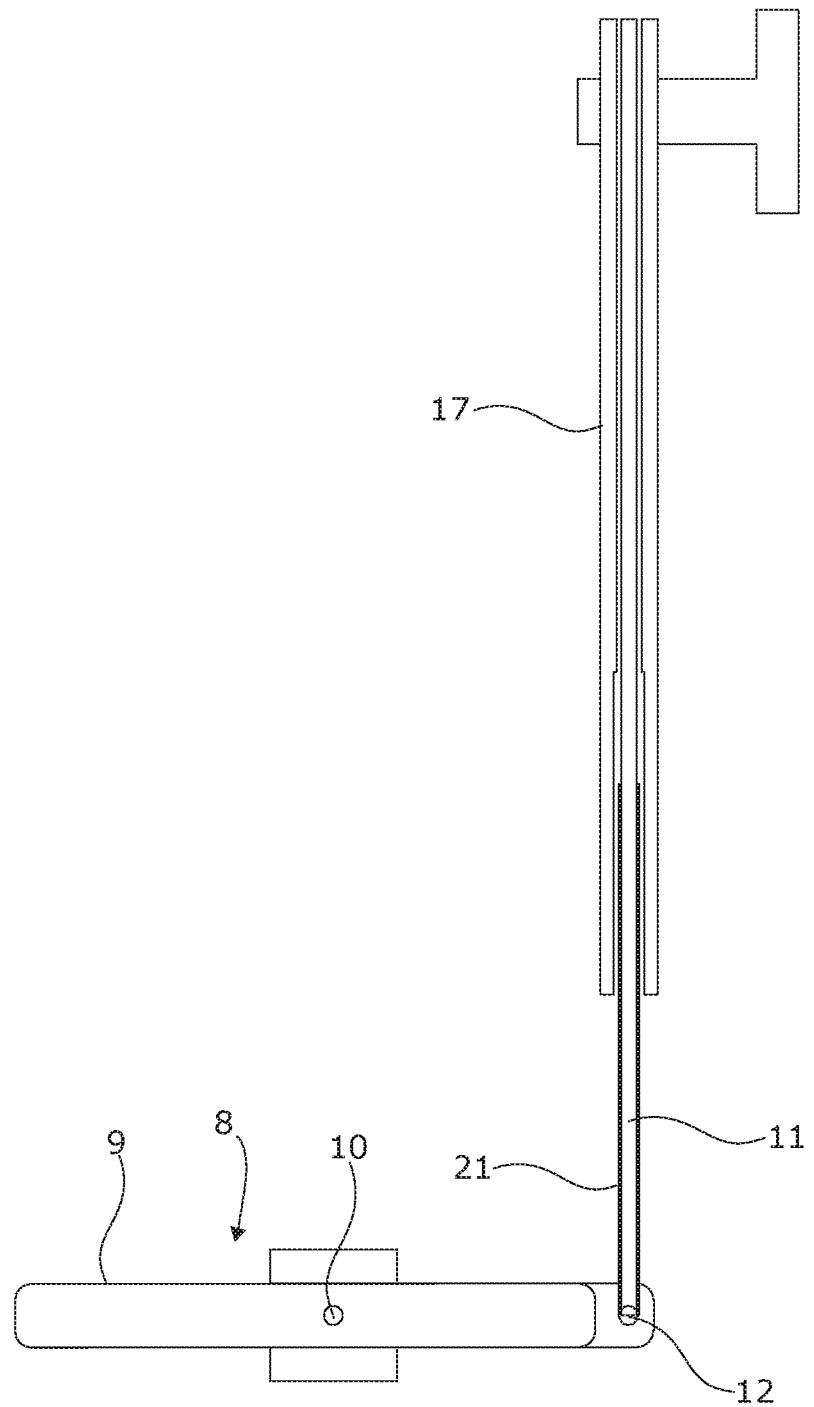

A further possible measure to prevent buckling is to provide the operating member 8 with a guide means as schematically shown in FIG. 7 as an external guide member 20 for the sheath 17. As can be seen the guide member is coaxially arranged with respect to both the sheath 17 and the elongated control member. By guiding the proximal end of the sheath 17 coaxially in the external guide member 20, the longitudinal axis of the elongated control member 11 and the proximal end of the sheath 17 are coaxially aligned during movement of the operating member 8 about the axis 10. This generally prevents the elongated control member 11 from buckling and allows it to be made thinner while buckling is still prevented when the operating member 11 is pushed into the sheath 17. The elongated control member 11, will thus not exert a lateral force on the rim 22 of the opening at the proximal end of the sheath 17. Accordingly, the sheath will be less prone to damage at the rim 22. The external guide member 20 is preferably made from a suitable plastic material. Alternatively, buckling of the proximal end of the elongated control member 11 may be prevented by providing the proximal end 11 of the elongated control member 11 with a guide means provided by an internal tubing 21 coaxially surrounding and the control member 11, as schematically shown in FIG. 8. As indicated by the schematic drawing of FIG. 8 this embodiment may also benefit of the presence of the external guide member 20. To ensure high rigidity of the internal tubing 21 it is preferably made of metal.

As mentioned above, the elongated control member 11 is preferably a steel rod, but in an alternative a tubular member could be used instead, in particular a steel tube. Providing such a steel tube with a narrow intermediate part 15 is simple in terms of manufacture as all it takes is to compress and flatten the desired intermediate part 15. This of course will provide a elongated control member 11 with a larger width at the intermediate part, and the width of the passages 14 should be adapted accordingly.

The skilled person will of course understand that there are numerous ways of providing an endoscope with a control member 11 with a narrower intermediate part according to the invention without departing from the invention as defined in the claims.

What is claimed is:

1. An endoscope having a proximal end and a distal end, said endoscope comprising:
   a handle at the proximal end;
   an operating member arranged at the handle;
   an insertion tube extending from the handle towards the distal end of the endoscope, said insertion tube terminating in a tip section at the distal end of the endoscope, the tip section comprising a bending section and an articulated tip part, the bending section comprising articulated segments and a most distal articulated segment extending distally from the articulated segments, each of said articulated segments comprising a guide passage; and
   an elongated control member having a proximal end, a distal end, and an intermediate section between the proximal end and the distal end, the proximal end of the elongated control member being attached to the operating member arranged at the handle,
   wherein the distal end of the elongated control member is attached to the most distal articulated segment of the bending section,
   wherein the intermediate section of the elongated control member passes through said guide passages and has a reduced cross-sectional area which is smaller than a cross-sectional area of a section of the elongated control member proximal of the intermediate section, and
   wherein the elongated control member comprises a tube with a collapsed part, wherein the collapsed part comprises the reduced cross-sectional area.

2. The endoscope of claim 1, wherein the distal end of the elongated control member also comprises a reduced cross-sectional area smaller than the cross-sectional area of the section of the elongated control member proximal of the intermediate section, said distal end being deformed to a predetermined shape for securing attachment with the most distal articulated segment.

3. The endoscope of claim 1, wherein the articulated tip part constitutes the most distal articulated segment of the bending section.

4. The endoscope of claim 1, wherein the elongated control member is made of metal.

5. The endoscope of claim 1, wherein the elongated control member comprises a rod.

6. The endoscope of claim 1, wherein a majority of a length of the elongated control member is covered with a coaxial sheath.

7. The endoscope of claim 6, wherein guide means are provided coaxially with the elongated control member and said coaxial sheath at or adjacent the proximal end of the elongated control member.

8. The endoscope of claim 7, wherein a working channel and the coaxial sheath are provided in the same integral member.

9. The endoscope of claim 1, wherein the elongated control member has a cross-section with a circular periphery having a diameter, from the proximal end to the intermediate section, and along the intermediate section has a cross-section with a height greater than the diameter and a width smaller than the diameter.

10. An endoscope having a proximal end and a distal end, said endoscope comprising:
    a handle at the proximal end;
    an operating member arranged at the handle;
    an insertion tube extending from the handle towards the distal end of the endoscope, said insertion tube terminating in a tip section at the distal end of the endoscope, the tip section comprising a bending section and an articulated tip part, the bending section comprising articulated segments and a most distal articulated segment extending distally from the articulated segments, each of said articulated segments comprising a guide passage; and
    an elongated control member having a proximal end, a distal end, and an intermediate section between the proximal end and the distal end, the proximal end of the elongated control member being attached to the operating member arranged at the handle,
    wherein the distal end of the elongated control member is attached to the most distal articulated segment of the bending section,
    wherein the intermediate section of the elongated control member passes through said guide passages and has a reduced cross-sectional area which is smaller than a cross-sectional area of a section of the elongated control member proximal of the intermediate section, and
    wherein the elongated control member has a cross-section with a circular periphery having a diameter, from the proximal end to the intermediate section, and along the intermediate section has a cross-section with a height equal to the diameter and a width smaller than the diameter.

11. An endoscope having a proximal end and a distal end, said endoscope comprising:
    a handle at the proximal end;
    an operating member arranged at the handle;
    an insertion tube extending from the handle towards the distal end of the endoscope, said insertion tube comprising a bending section having articulated segments and a most distal articulated segment extending distally from the articulated segments, each of said articulated segments comprising a guide passage having a cross-section with a height and a width, wherein the height is larger than the width; and an elongated control member having a proximal end, a distal end, and an intermediate section between the proximal end and the distal end, the intermediate section having a cross-section corresponding to the cross-section of the guide passages, and the elongated control member having a cross-section along the proximal end with a height and a width, wherein the height is equal to the width.

12. The endoscope of claim 11, wherein the cross-section of the elongated control member along the distal end has a substantially circular periphery.

13. The endoscope of claim 12, wherein the elongated control member has a cross-section along the proximal end which is equal to a cross-section of the elongated control member at the distal end.

14. The endoscope of claim 11, wherein the cross-section of the intermediate section is equal to a cross-section of the distal end of the elongated control member.

15. The endoscope of claim 11, further comprising a sheath enclosing a portion of the elongated control member proximal of the intermediate section, and an external guide member positioned in the handle slidably receiving a proximal end of the sheath and configured to longitudinally translate the elongated control member within the sheath.

* * * * *